(12) United States Patent
Faivre et al.

(10) Patent No.: US 9,757,337 B2
(45) Date of Patent: Sep. 12, 2017

(54) MULTICOMPARTMENTAL LIPID NANOPARTICLES

(71) Applicants: CENTRE NATIONAL DE LA RECHERCHE SCIENTIFIQUE—CNRS, Paris (FR); UNIVERSITE PARIS-SUD, Orsay (FR)

(72) Inventors: Vincent Faivre, Paris (FR); Sylviane Lesieur, Sceaux (FR); Michel Ollivon, Fontenay-sous-Bois (FR); Modibo Ouattara, Abidojan (CI); Tri Truong Cong, Ho Chi Minh (VN)

(73) Assignees: CENTRE NATIONAL DE LA RECHERCHE SCIENTIFIQUE—CNRS, Paris (FR); UNIVERSITE PARIS-SUD, Orsay (FR)

( * ) Notice: Subject to any disclaimer, the term of this patent is extended or adjusted under 35 U.S.C. 154(b) by 0 days.

(21) Appl. No.: 14/907,249

(22) PCT Filed: Jul. 24, 2014

(86) PCT No.: PCT/FR2014/051922
§ 371 (c)(1),
(2) Date: Jan. 22, 2016

(87) PCT Pub. No.: WO2015/011419
PCT Pub. Date: Jan. 29, 2015

(65) Prior Publication Data
US 2016/0158153 A1    Jun. 9, 2016

(30) Foreign Application Priority Data

Jul. 25, 2013  (FR) ...................... 13 57363

(51) Int. Cl.
*A61K 9/127*   (2006.01)
*B01J 13/02*   (2006.01)
(Continued)

(52) U.S. Cl.
CPC .......... *A61K 9/1271* (2013.01); *A61K 9/1277* (2013.01); *A61K 31/055* (2013.01);
(Continued)

(58) Field of Classification Search
None
See application file for complete search history.

(56) References Cited

U.S. PATENT DOCUMENTS 5,576,016 A    11/1996  Amselem et al.
5,662,932 A *  9/1997   Amselem ............. A61K 9/1075
                                                     424/45

(Continued)

FOREIGN PATENT DOCUMENTS

WO          0164328 A1    9/2001

OTHER PUBLICATIONS

JN Israelachvili, S Marcelja, RG Horn. "Physical principles of membrane organization." Quarterly Reviews of Biophysics, vol. 13(2), 1980, pp. 121-200.*

(Continued)

*Primary Examiner* — Isaac Shomer
(74) *Attorney, Agent, or Firm* — Cantor Colburn LLP

(57) ABSTRACT

The present invention relates to novel multicompartmental lipid nanoparticles (or cellisomes) with excellent stability comprising a first lipophilic compartment (lipid matrix) partly anchored to a second hydrophilic compartment delimited by a phospholipid bilayer (bilayer), as well as the method for preparing same and the use thereof as a vector for administering a wide variety of molecules of interest.

21 Claims, 9 Drawing Sheets

(51) Int. Cl.
  *A61K 31/055*  (2006.01)
  *A61K 31/09*  (2006.01)
  *A61K 31/353*  (2006.01)
  *A61K 31/522*  (2006.01)

(52) U.S. Cl.
  CPC ............ *A61K 31/09* (2013.01); *A61K 31/353* (2013.01); *A61K 31/522* (2013.01); *B01J 13/02* (2013.01); *Y10S 977/773* (2013.01); *Y10S 977/906* (2013.01); *Y10S 977/907* (2013.01)

(56) References Cited

U.S. PATENT DOCUMENTS

| | | | |
|---|---|---|---|
| 5,853,755 | A * | 12/1998 | Foldvari ............... A61K 9/0014 264/4.1 |
| 2010/0099646 | A1* | 4/2010 | Kachi .................... A61Q 19/00 514/54 |

OTHER PUBLICATIONS

H Teixeira, C Dubernet, V Rosilio, S Benita, J Lepault, I Erk, P Couvreur. "New Biocompartmental Structures Are Observed When Stearylamine is Mixed with Triglyceride Emulsions." Pharmaceutical Research, vol. 17, No. 10, 2000, pp. 1329-1332.*

B Marten, M Pfeuffer, J Schrezenmeir. "Medium-chain triglycerides." International Dairy Journal, vol. 16, 2006, pp. 1374-1382.*

G Fricker, T Kromp, A Wendel, A Blume, J Zirkel, H Rebmann, C Setzer, R-O Quinkert, F Martin, C Mueller-Goymann. "Phospholipids and Lipid-Based Formulations in Oral Drug Delivery." Pharmaceutical Research, vol. 27, 2010, pp. 1469-1486.*

Beatrice Heurtault et al. "A Novel Phase Inversion-Based Process for the Preparation of Lipid Nanocarriers", Pharmaceutical Research; Jun. 1, 2002; vol. 19, No. 6, pp. 875-880; XP002539234.

H. Heiati et al. "Evidence for phospholipid bilayer formation in solid lipid nanoparticles formulated with phospholipid and triglyceride" Pharmaceutical research; Sep. 1, 1996; pp. 1406-1410; XP055108356.

International Search Report issued Sep. 3, 2014 re: Application No. PCT/FR2014/051922; pp. 1-3; citing: US 5 662 932 A, H. Heiati et al. and Beatrice Heartault et al.

Eliana B. Souto et al. "Solid Lipid Nanoparticle Formulations: Pharamacokinetic and Biopharmaceutical Aspects in Drug Delivery" Methods in Enzymology, 2009, vol. 464, pp. 105-129.

Gert Storm et al. "Liposomes: quo vadis?", Pharmaceutical Science & Technology Today, Apr. 1998, vol. 1, No. 1, pp. 19-31.

Harshad Harde et al. "Solid lipid nanoparticles: an oral bioavailability enhancer vehicle" Expert Opinion on Drug Delivery, url://www.informahealthcare.com by Niper 2011, vol. 8, No. 11, pp. 1407-1424.

Heike Bunjes "Structural properties of solid lipid based colloidal drug delivery systems", Current Opinion in Colloid & Interface Science, Science Direct, 2011, vol. 16, No. 5pp. 405-511.

Helder Teixeira et al. "New Biocompartmental Structures Are Observed When Stearylamine is Mixed with Triglyceride Emulsions", Pharmaceutical Research, 2000, vol. 17, No. 10, pp. 1329-1332.

Henry Yim Wu et al. "Mucosal Anti-CD3 Monoclonal Antibody Attenuates Collagen-Induced Arthritis That is Associated with Induction of LAP+ Regulatory T Cells and is Enhanced by Administration of an Emulsome-Based Th2-Skewing Adjuvant", Journal of Immunol.

Jana Pardeike et al. "Lipid nanoparticles (SLN, NLC) in cosmetic and pharmaceutical dermal products" Internationa Journal of Pharmaceutics, 2009, vol. 366, pp. 170-184.

Louise A. Meure et al. "Conventional and Dense Gas Techniques for the Production of Liposomes: A Review", AAPS PharmSciTech, Sep. 2008, vol. 9, No. 3, pp. 798-809.

M. Harms et al. "Solid lipid nanoparticles for drug delivery" Journal of Drug Delivery Science and Technology, 2011, vol. 21, No. 1, pp. 89-99.

M. Kretschmar et al. Efficient treatment of murine systemic infection with Candida albicans using amphotericin B incorporated in nanosize range particles (emulsomes), MYCOSES, 2001, vol. 44, pp. 281-286.

Medha D. Joshi et al. "Lipid nanoparticles for parenteral delivery of actives" European Journal of Pharmaceutics and Biopharmaceutics, 2009, vol. 71, pp. 161-172.

N.T. Huynh et al. "Lipid nanocapsules: A new platform of nanomedicine" International Journal of Pharmaceutics, 2009, vol. 379, pp. 201-209.

Rainer H. Muller et al. "20 Years of Lipid Nanoparticles (SLN & NLC): Present State of Development & Industrial Applications" Current Drug Discovery Technoligies, 2011, vol. 8, No. 3, pp. 207-227.

Rishi Paliwal et al. "Engineered chylomicron mimicking carrier emulsome for lymph targeted oral delivery of methotrexate" International Journal of Pharmaceutics, 2009, vol. 380, pp. 181-188.

Swati Gupta et al. "Antileishmanial efficacy of amphotericin B bearing emulsomes against experimental visceral leishmaniasis" Journal of Drug Targeting, Informa healthcare, 2007, vol. 15, No. 6, pp. 437-444.

Swati Gupta et al. "Development and characterization of amphotericin B bearing emulsomes of passive and active macrophage targeting" Journal of Drug Targeting, Apr. 2007, vol. 15, No. 13, pp. 206-217.

\* cited by examiner

MULTICOMPARTMENTAL LIPID NANOPARTICLES

FIELD OF THE INVENTION

The present invention should be seen in the context of the development of nanotechnologies for administering active principles.

The present invention relates to multicompartment lipid nanoparticles, (hereinafter called "cellisomes"), the preparation method thereof and the use of same as carriers for administering molecules of interest, in particular by injection, orally, nasally or cutaneously.

In the description below, the references in square brackets ([ ]) refer to the list of references presented at the end of the text.

BACKGROUND

During the last 30 years, two main categories of nanometer-scale systems have been developed for use as carriers for molecules of interest: polymer systems and lipid systems.

The first of these were shown to be relatively disappointing in terms of their industrial application, likely for reasons of toxicity. Furthermore, the formulations available on the market are predominantly based on lipids that have generated two large families of carriers: liposomes and lipid particles (nanoemulsions (NE), nanostructured lipid carriers (NLC), solid lipid nanoparticles (SLN)). Liposomes, and to a lesser extent nanoemulsions, have given rise to numerous cosmetic applications and several medicines on the market, while nanostructured or solid lipid particles, developed more recently, are present in many cosmetic products and in clinical trials for the pharmaceutical sector.

A liposome is defined as an artificial structure consisting of one or more concentric lipid bilayers, confining between them compartments of water or aqueous buffer. Liposomes are prepared from a single type, or from several types, of natural or synthetic phospholipids organized such that the polar heads come together so as to create the bilayer. The most traditional method of preparing liposomes is so-called lipid film hydration. Liposomes are increasingly being developed as carriers for hydrosoluble, liposoluble and amphiphilic active principles. The encapsulation of active principles in the aqueous phase or the lipid bilayer thus makes it possible to protect said principles from enzymatic degradation or elimination by the immune system, but also to decrease their possible toxic side effects (e.g., hemolysis, thrombophlebitis, blood coagulation) when administered parenterally. (Meure et al., Aaps Pharmscitech, 9:798-809, 2008; Storm and Crommelin, Pharmaceutical Science & Technology Today, 1:19-31, 1998) [1, 2]. At the root of a dozen commercial compositions (e.g., Myocet®, Doxil®/Caelyx®, AmBisome®, Visudyne®, etc.), liposomes have several major disadvantages, however: they lack specificity for the target cell, the oxidation and physical instability of phospholipids requires them to be lyophilized, they are delicate to produce industrially, and there is a certain limit to the amount of molecules of interest that can be encapsulated. Indeed, amphiphilic or lipophilic molecules are able to combine with liposomes by insertion into their membranes, but at the risk of destabilization of the latter.

Emulsions are fine dispersions of droplets of one liquid (dispersed phase) in another (dispersant or continuous phase), the two liquids being relatively immiscible; they are most often of the water/oil type. The term "nanoemulsion" (NE) is used when the particle size obtained is very small, i.e., a mean size of about a hundred nanometers. They are generally produced by mechanical fragmentation of an oil phase in an aqueous phase, and optionally stabilized by the presence of surfactant. Compared to conventional emulsions, the small size of the globules gives them advantageous pharmaceutical properties, in particular in terms of physical stability during storage and possible routes of administration, in particular intravenous administration requiring the use of small droplets. However, these systems can incorporate only very lipophilic active principles that are soluble in the component oils of these emulsions (soybean oil, olive oil), thus limiting their potential applications.

Solid lipid nanoparticles (SLN) and nanostructured lipid carriers (NLC) were developed to increase the physicochemical stability of encapsulated active principles and the post-administration stability of lipid carriers as a whole, generally for eventual use in cosmetics, by virtue of their properties of adhesion, occlusion and skin hydration, and in pharmaceuticals for administering and protecting active principles of interest. (Bunjes, Current Opinion in Colloid & Interface Science, 16(5):405-411, 2011; Harde et al., Expert Opinion on Drug Delivery, 8(11):1407-1424, 2011; Harms et al., Journal of Drug Delivery Science and Technology, 21(1):89-99, 2011; Joshi and Muller, European Journal of Pharmaceutics and Biopharmaceutics, 71:161-172, 2009; Muller et al., Current Drug Discovery technologies, 8(3): 207-227, 2011; Pardeike et al., International Journal of Pharmaceutics, 366:170-184, 2009; Souto and Doktorovova, Methods in Enzymology, 464:105-129, 2009) [3-9]. As with the nanoemulsions described above, the very high lipophilicity of the raw materials used limits the choice of potentially administrable active principles. Moreover, it was shown that the polymorphism of lipids in the solid state has a large influence on the physical stability of these systems (expulsion of active molecules, gelation), in particular in the case of SLN.

Lipid nanocapsules developed by the University of Angers were obtained by a phase-inversion method and are surrounded by a phospholipid monolayer. Although very similar to SLN and NLC type nanodispersions, these particles have been described as nanocapsules stabilized by a crystallized layer of phospholipids and a nonionic polyoxyethylene surfactant (international application WO 01/64328; Huynh et al., Journal of Pharmaceutics, 379:201-209, 2009) [10, 11]. Advantageous because it is relatively "mild," the phase-inversion technique requires the use of relatively specific raw materials and very fine control of temperatures during the preparation process. These aspects can limit the large-scale development of this approach.

A few years ago, submicron-scale cationic emulsions consisting of two-compartment oil/water structures, called "handbags," were developed (FIG. 1). In order to use them as carriers for active principles, their formation requires the presence of stearylamine, which supports the mass insertion of triglycerides into the lipid bilayer delimiting the aqueous compartment (Texeira et al., Pharmaceutical Research, 17:1329-1332, 2000) [12]. Unfortunately, the proportion of these two-compartment objects remains in the minority (less than 20%) among a multitude of other objects formed during the preparation process (micelles, liposomes, nanoemulsions). Moreover, the use of a cationic surfactant like stearylamine should be considered with caution considering the toxicity of this type of product to negatively-charged biological membranes.

More marginal, nanoemulsions of particles having a diameter of 10-250 nm (called emulsomes or ultrasomes)

comprising a lipid core consisting of a lipid in liquid or solid form surrounded and stabilized by at least one phospholipid bilayer, as in liposomes, were developed and designed for the parenteral, oral, rectal, intranasal or topical administration of liposoluble or hydrosoluble molecules (U.S. Pat. No. 5,576,016; Gupta et al., Journal of Drug Targeting, 15:437-444, 2007; Gupta and Vyas, Journal of Drug Targeting, 15:206-217, 2007; Kretschmar et al., Mycoses, 44:281-286, 2001; Paliwal et al., International Journal of Pharmaceutics, 380:181-188, 2009; Wu et al., Journal of Immunology, 185(6):3401-3407, 2010) [13-18]. The method for preparing these emulsomes is applied with difficulty on an industrial scale because it generally requires the use of an organic solvent and the deposition and rehydration of a phospholipid film. Indeed, these particles are mainly obtained by a phospholipid film hydration technique very similar to that employed for liposomes, except that the aqueous phase contains preformed lipid nanoparticles. The final particle results from the "statistical confinement" of oil droplets in the phospholipid bilayers. Consequently, the process generates a priori various populations of objects (emulsomes, liposomes, nanoemulsions or solid nanoparticles) with no uniting of the lipid and phospholipid parts. This can a priori cause system stability problems during certain purification operations (centrifugation, for example) or during storage.

There is thus a genuine need for lipid carriers that sweep aside these defects, disadvantages and obstacles of the prior art, in particular for a simple production method making it possible to control the long-term stability of lipid carriers for administering a large amount of molecules of interest having a wide range of polarity and, optionally, to envisage the co-encapsulation of hydrophilic and lipophilic active principles in the same nano-object

BRIEF SUMMARY

Based on their own experiences with the stability and toxicity of lipid nanosystems, the Inventors have developed novel multicompartment lipid nanoparticles (or cellisomes) representing a hybrid system between those described above, namely liposomes and lipid particles (FIGS. 2A-B), in which a lipid matrix and an aqueous compartment are combined within the same nanometer-scale object. The principal novelty of the cellisomes of the invention comes from their multicompartment morphology (FIG. 3) despite a simple preparation method (high-pressure homogenization) applicable at an industrial scale. Furthermore, the raw materials used are relatively inexpensive, already recognized by various pharmacopoeias, and employed in the pharmaceutical industry.

Morphologically, these multicompartment nanoparticles of the invention are completely different from emulsomes. In the latter, the object is isotropic (from the center, the same properties in all directions) because the lipid compartment is incorporated within one or more phospholipid bilayers, themselves delimiting concentric aqueous compartments. In the case of the multicompartment lipid nanoparticles (cellisomes) of the invention, the organization is anisotropic (from the center, the properties are different depending on the direction) because the lipid compartment is only partially covered by the aqueous compartment.

In the cellisomes of the invention, the lipid core can consist of lipid mixtures that are liquid or semi-solid at room temperature (25° C.) and that incorporate glycerides and polyethylene glycol esters. The latter aspect is very important in terms of enabling the encapsulation within said nanoparticles of active principles (AP) having a wide range of polarity (AP lipophilic in glycerides, AP more hydrophilic in polyethylene glycols).

Moreover, unlike what is observed for many drug carriers, the stability of suspensions of cellisomes of the invention extends to several tens of months without the need of a lyophilization step as in the case with liposomes, for example. The cellisomes of the invention are stabilized with a mixture of surfactants containing phospholipids (e.g., Phospholipon® 90G) and mixtures of nonionic surfactants including some of the "hydrophobic-hydrophilic-hydrophobic" type having a Griffin HLB of greater than 11. These three-sequence surfactants can, for example, belong to the family of macrogolglycerides (e.g., Gelucire® 50/13) or of polyoxyethylene fatty acids (e.g., polyoxyethylene 40 stearate). This mixture of surfactants has previously shown its advantage in the long-term stabilization of cocoa butter nanoparticles (more than 4 years), and the very low toxicity of the latter was shown in a colorimetric assay using tetrazolium salt (MTT). The mixing and treatment of these excipients according to the protocol described below produces the cellisomes of the invention, preferably in the case of a lipid phase made of linoleoyl polyoxylglycerides and/or oeyl polyoxylglycerides (Labrafil®), clearly different from the image of a typical nanoemulsion (NE).

Furthermore, measurements of the thickness of the outer layer, dark and thus dense with electrons, strongly suggest a first lipophilic compartment (lipid matrix or core) partly enclosed by a second hydrophilic compartment delimited by a phospholipid bilayer (bilayer). Moreover, the study of the structure of the cellisomes of the invention shows that said first compartment is partly anchored to said second compartment due to the use of suitable nonionic surfactants such as those described above. Without being limited by this explanation, it would seem that the architectural keystone of the cellisomes of the invention rests on the use of a hydrophilic nonionic surfactant mixture containing at least one three-segment derivative of the "hydrophobic-hydrophilic-hydrophobic" type. The hydrophobic segments can consist of fatty alcohols, fatty acids, glycerides, cholesterol or any other group with affinity for phospholipid membranes. The hydrophilic part will consist of polymers of the polyoxyethylene, polypropylene, polysaccharide type, or any type of polymer able to generate, in association with the hydrophobic segments, surfactants having an HLB value of greater than 11. HLB is defined herein according to the scale described by Griffin. These surfactants may, for example, belong to the family of polyoxylglycerides or macrogolglycerides, of polyoxyethylene fatty acid esters or of polyoxyethylene alkyl ethers, preferably will be Gelucire 50/13 or polyoxyethylene (40) stearate. Polyoxyethylene fatty acid esters are mixtures of fatty acids esterified with a hydrophilic poly(oxyethyleneglycol) chain, and contain a mixture, in a variable proportion, of derivatives sequenced with two blocks of the fatty acid-PEG type (monoesters) and derivatives sequenced with three blocks of the fatty acid-PEG-fatty acid type (diesters). Macrogolglycerides also contain glycerides. In particular, Gelucire® 50-13 is a mixture of glycerides and fatty acid esterified with a 1500 g/mol hydrophilic poly(oxyethyleneglycol) chain, which contains about 40% derivatives sequenced with three blocks of the fatty acid-PEG-fatty acid type (FIG. 4A). In the proposed system, the diester fraction is most certainly the anchor point between the bilayer and the lipid part (FIG. 4B). Indeed, it is known in the art that the incorporation of phospholipids into a lipid particle-type formulation generally results in heterogeneous preparations containing two types of objects, nanoparticles and liposomes. The same result was obtained by applying the experimental protocol of the invention in the absence of nonionic surfactants of the "hydrophobic-hydrophilic-hydrophobic" type having a Griffin HLB value of greater than 11 (data not shown). In the proposed system, the fraction of these surfactants is most certainly the anchor point between the bilayer and the lipid part (FIG. 4B).

The present invention thus has as an object multicompartment lipid nanoparticles (cellisomes) having a mean diameter of about 10 to 500 nm, characterized in that they comprise a first lipophilic compartment partly enclosed by a second hydrophilic compartment delimited by a phospholipid bilayer, said first compartment being partly anchored to said second compartment.

According to a specific embodiment of the present invention, the cellisomes of the invention have a polydispersity index (i.e., the size distribution of a population of particles) of about 5 to 15%, preferably of 10%.

Preferably the cellisomes of the invention have a mean diameter of about 100 to 250 nm.

According to a particular embodiment of the invention, the lipophilic compartment of the cellisomes of the invention consists of lipids in the liquid or semi-solid state at room temperature. Preferably, said lipophilic compartment essentially consists of a fatty acid ester optionally mixed with a glyceride.

Preferably said fatty acid ester is selected from the group consisting of mixtures of polyethylene glycol mono- and diesters the molar mass of the hydrophilic part of which varies from 100 to 700 g/mol.

Preferably the glyceride is selected from the group consisting of mixtures of glycerol mono-, di- and triesters that are liquid or solid at room temperature.

According to a particular embodiment of the invention, the phospholipid bilayer of the cellisomes of the invention consists essentially of phospholipid and hydrophilic nonionic surfactant.

Preferably said phospholipid is selected from the group consisting of mixtures of essentially zwitterionic phospholipids.

Preferably said nonionic surfactant is selected from the group consisting of a hydrophilic nonionic surfactant mixture containing at least one three-segment derivative of the "hydrophobic-hydrophilic-hydrophobic" type. The hydrophobic segments can consist of fatty alcohols, fatty acids, glycerides, cholesterol or any other group with affinity for phospholipid membranes. The hydrophilic part will consist of polymers of the polyoxyethylene, polypropylene or polysaccharide type, or any type of polymer able to generate, in association with the hydrophobic segments, surfactants having an HLB value of greater than 11. HLB is defined herein according to the scale described by Griffin. These surfactants may, for example, belong to the family of polyoxylglycerides or macrogolglycerides, of polyoxyethylene fatty acid esters or of polyoxyethylene alkyl ethers, preferably will be Gelucire 50/13 or polyoxyethylene (40) stearate.

The present invention also has as an object multicompartment lipid nanoparticles (cellisomes) of the invention further comprising at least one molecule of interest.

Preferably the molecule of interest is selected from a nucleic acid, a protein, a polysaccharide, a small molecule or any other molecule of pharmaceutical, cosmetic and/or food-processing interest.

By "small molecule" is meant, in the context of the present invention, for example, molecules having a molecular mass of 60 to 5000 Da, preferably of 40 to 3000 Da, most preferably of less than 2000 Da.

The present invention also has as an object a pharmaceutical composition comprising a suspension of multicompartment lipid nanoparticles (cellisomes) of the invention in a pharmaceutically acceptable excipient.

The present invention also has as an object a method for preparing the multicompartment lipid nanoparticles (cellisomes) of the invention comprising the following steps:
  preparation of an oil/water emulsion comprising at least one lipid, one phospholipid, one hydrophilic nonionic surfactant, and optionally at least one molecule of interest;
  homogenization of said emulsion under high pressure.

According to a particular embodiment of the invention, said method of the invention further comprises a step of heating the emulsion to a temperature of 30 to 80° C., preferably to 70° C., before its homogenization.

Preferably said lipid is selected from the group consisting of mixtures of polyethylene glycol mono- and diesters the molar mass of the hydrophilic part of which varies from 100 to 700 g/mol.

Preferably said phospholipid is selected from the group consisting of mixtures of essentially zwitterionic phospholipids.

Preferably said hydrophilic nonionic surfactant is selected from the group consisting of the family of polyoxylglycerides or macrogolglycerides, of polyoxyethylene fatty acid esters or of polyoxyethylene alkyl ethers, preferably Gelucire® 50/13 or polyoxyethylene (40) stearate.

Preferably the oil/water emulsion of the method of the invention comprises:
  5-30% lipids, preferably Labrafil® M2125CS or M1944CS,
  0.5-5% phospholipids, preferably Phospholipon 90G®;
  0.5-5% macrogolglycerides or polyoxyethylene fatty acid esters, preferably Gelucire® 50-13 or polyoxyethylene (40) stearate;
  Water, q.s. ad 100 g.

The "%" symbols refer to % of the total mass of the emulsion.

The present invention also has as an object the multicompartment lipid nanoparticles (cellisomes) of the invention for use as a carrier for administering a molecule of interest.

The present invention also has as an object the multicompartment lipid nanoparticles (cellisomes) of the invention for use as a medicine, preferably a medicine administered by injection, orally, nasally or cutaneously.

Other advantages will become apparent to the skilled person on reading the examples below, illustrated by the appended figures, provided for purposes of illustration.

DETAILED DESCRIPTION AND EXAMPLES

Example 1: Preparation of Multicompartment Lipid Nanoparticles (Cellisomes)

Preparation

Figure 5:
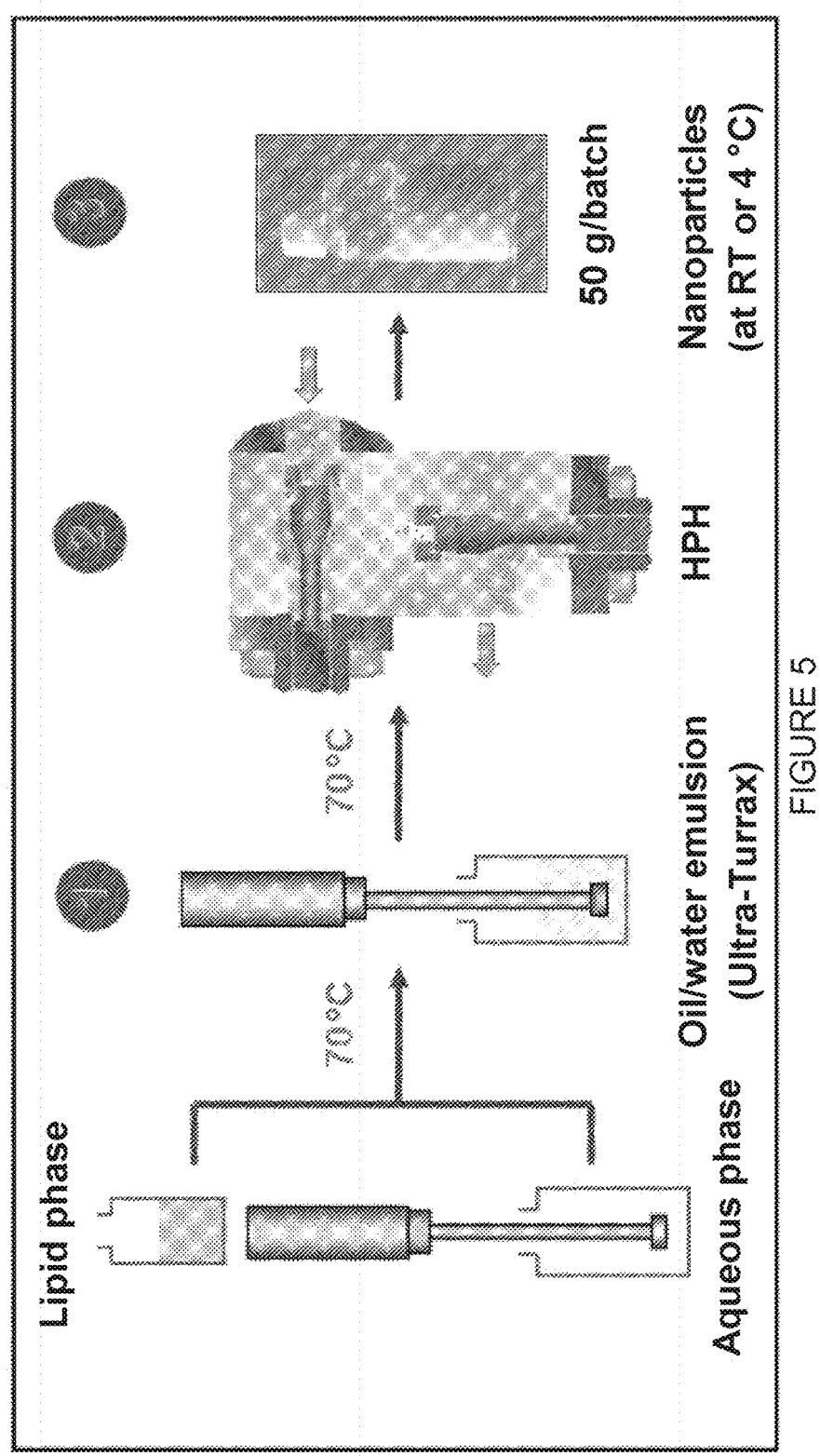
FIG. 5 shows a diagram for preparing the multicompartment lipid nanoparticles of the invention.

The preparation of multicompartment lipid nanoparticles is depicted schematically in FIG. 5.

Nanodispersions were prepared using a two-stage homogenizer (APV 2000, Invensys, Albertslund, Denmark) fitted with a heating system and associated with a T25 Ultra-Turrax (Janke & Kunkel GmbH & Co.KG, IKA®-Labotechnik, Germany) for preparation of the primary emulsion.

For each batch, 50 g of nanodispersions was prepared according to the protocol including the following three steps:

Dispersion:

First, the lipids and the surfactants (Gelucire® 50/13 and Phospholipon® 90G) were weighed and introduced into 20 ml and 100 ml flasks, respectively. The required amount of water was added to the flask containing the surfactants and then the surfactant suspension was prepared at 70° C. with mechanical agitation (T25 Ultra-Turrax, Janke & Kunkel GmbH & Co.KG, IKA®-Labotechnik, Germany) at a speed of 9500 rpm for 5 minutes. Finally, the lipid mixture, also heated to 70° C., was added to the aqueous phase and agitated with the Ultra-Turrax at a speed of 13500 rpm for 5 minutes, to produce an oil/water predispersion.

Particle Size Reduction and Homogenization Using HPH:

The predispersion obtained was quickly introduced into the two-stage homogenizer (APV 2000, Invensys, Albertslund, Denmark) preheated to 70° C. It underwent therein several continuous homogenization cycles for 5 minutes, under a double effect of pressure (the pressure of the $1^{st}$ stage is 600 bar and that of the $2^{nd}$ stage is 200 bar), to form a hot oil/water nanoemulsion.

Cooling the Particles:

The nanodispersions were then maintained at room temperature and at 4° C.

Composition

The multicompartment lipid nanoparticles obtained by the preparation method described above comprise for example:

| | |
|---|---|
| Lipids (Labrafil ®) | 5 to 20% |
| Phospholipids (Phospholipon 90G) | 1% |
| Macrogolglycerides (Gelucire ® 50-13) | 2% |
| Water (q.s. ad) | 100 g |

Stability of the Multicompartment Lipid Nanoparticles

The storage at room temperature of the multicompartment lipid nanoparticles suspended in water was monitored over several months, as to their size and polydispersity. An example of this monitoring was shown for Labrafil® M 2125 CS. The standard deviation of the mean diameter (n=3) generally masked by the symbol, confirmed the good reproducibility of the method. The nanoparticle diameter of less than 200 nm is suited to intravenous administration. The polydispersity of less than 0.2 expresses a narrow size distribution around the mean.

Figure 6:
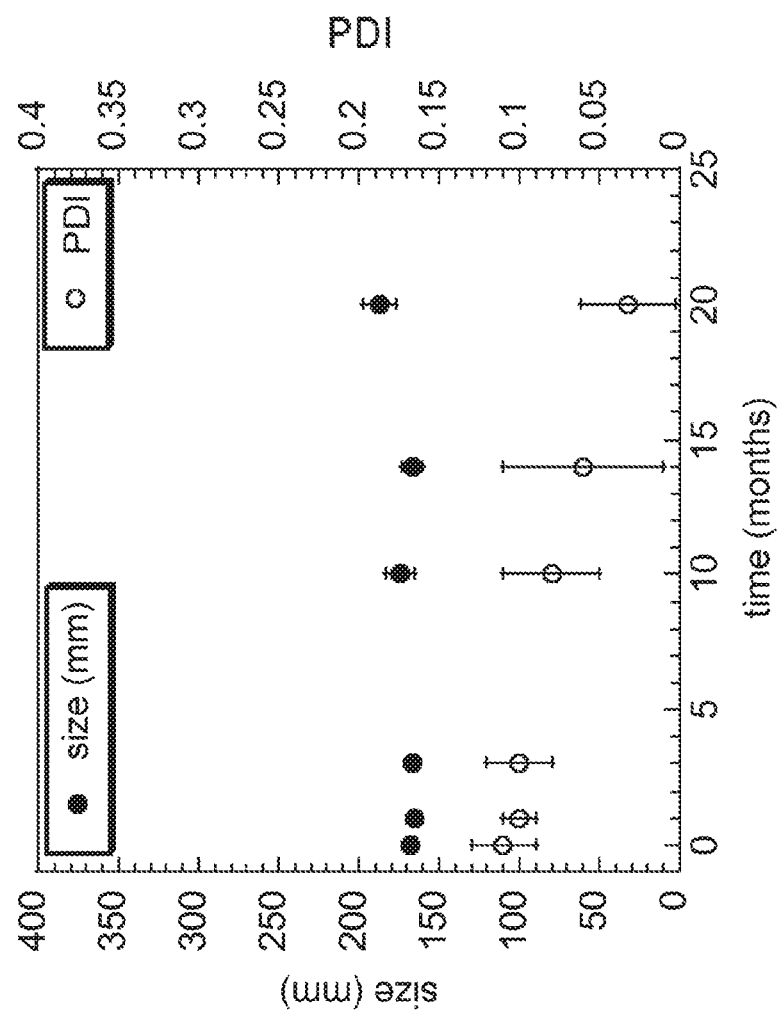
FIG. 6 shows the monitoring over 20 months of the size of the multicompartment lipid nanoparticles and their polydispersity for Labrafil® M 2125 CS

Suspended in water, the oldest multicompartment lipid nanoparticles retained an identical diameter (170-180 nm) and polydispersity (~0.1) for more than 20 months (FIG. 6).

Example 2: Multicompartment Lipid Nanoparticles (Cellisomes) as Carriers for Quercetin Preparation of Multicompartment Lipid Nanoparticles as Carriers for Active Principles The multicompartment lipid nanoparticles obtained by the protocol above were tested for their ability to encapsulate pharmaceutical active principles.

To this end, for example, studies were carried out on the encapsulation of quercetin. This active principle has the twin disadvantage of being relatively insoluble in water (~0.4 μg/ml) and quickly hydrolyzed under certain pH conditions. The advantages of encapsulation were thus studied with regard to these two points.

Particles were prepared according to the protocol described above, by dissolving to saturation the active principle in the lipid phase before its emulsification in the aqueous phase containing the surfactants. Unencapsulated active principle was separated by ultracentrifugation (Optima LE-80K Ultracentrifuge, 30000 rpm, 1 h, 4° C.) and then the encapsulated fraction was assayed in the supernatant, which contains the nanoparticles, by high-performance liquid chromatography (HPLC) according to a method developed in the laboratory. Namely, quercetin was assayed using a Waters™ HPLC device fitted with a UV detector (Waters™ 2487 Dual λ Absorbance Detector), a pump (Waters™ 1525 Binary HPLC Pump), an injector combined with an automatic sample transport system (Waters™ 717 Plus Autosampler) and an in-line degasser (Waters™ In-line Degasser AF). The separation was carried out on a column (Modulo-cart QK 3 C18-2 columns, 150 mm×3 mm, Interchim) at 25° C. with a mobile phase of acetonitrile-water-trifluoroacetic acid (30:70:0.1, v/v). The wavelength of the detector was set at 371 nm. The flow rate was 0.5 ml/min and the injection volume 20 μl. The standard range established from three independent stock solutions and containing white lipid particles had a correlation coefficient ($r^2$) of 0.9998 and a wide region of linearity of 50 to 5000 ng/ml. These figures confirmed that the specificity, sensitivity and precision of the method were high under the given chromatographic conditions. Before being analyzed by HPLC, all the samples were dissolved in methanol at concentrations within the linear range and then filtered through a membrane of 0.2 μm mean porosity (Minisart® High-Flow Hydrophilic 16532K, Sartorius Stedim Biotech GmbH, Goettingen, Germany). The HPLC method developed makes it possible to separate the AP and the excipients, and thus to directly determine the AP content encapsulated in the lipid particles and the stability and release kinetics in the various dissolution media.

The maximum load of active principle in the suspension is about 1% (or $5·10^3$ times its aqueous solubility) with an encapsulation yield of about 96% under optimal conditions.

In addition, it became apparent that the presence of PEG on the surface of the nanoparticles enables them a priori to benefit from the property of stealth (escape capture by the reticuloendothelial system) widely described for "PEGylated" liposomes and essential to their administration in vivo.

Stability of Free or Encapsulated Quercetin

The stability of quercetin, hydrolyzed in aqueous medium and encapsulated in the multicompartment lipid nanoparticles of the invention, was tested.

Figure 7A:
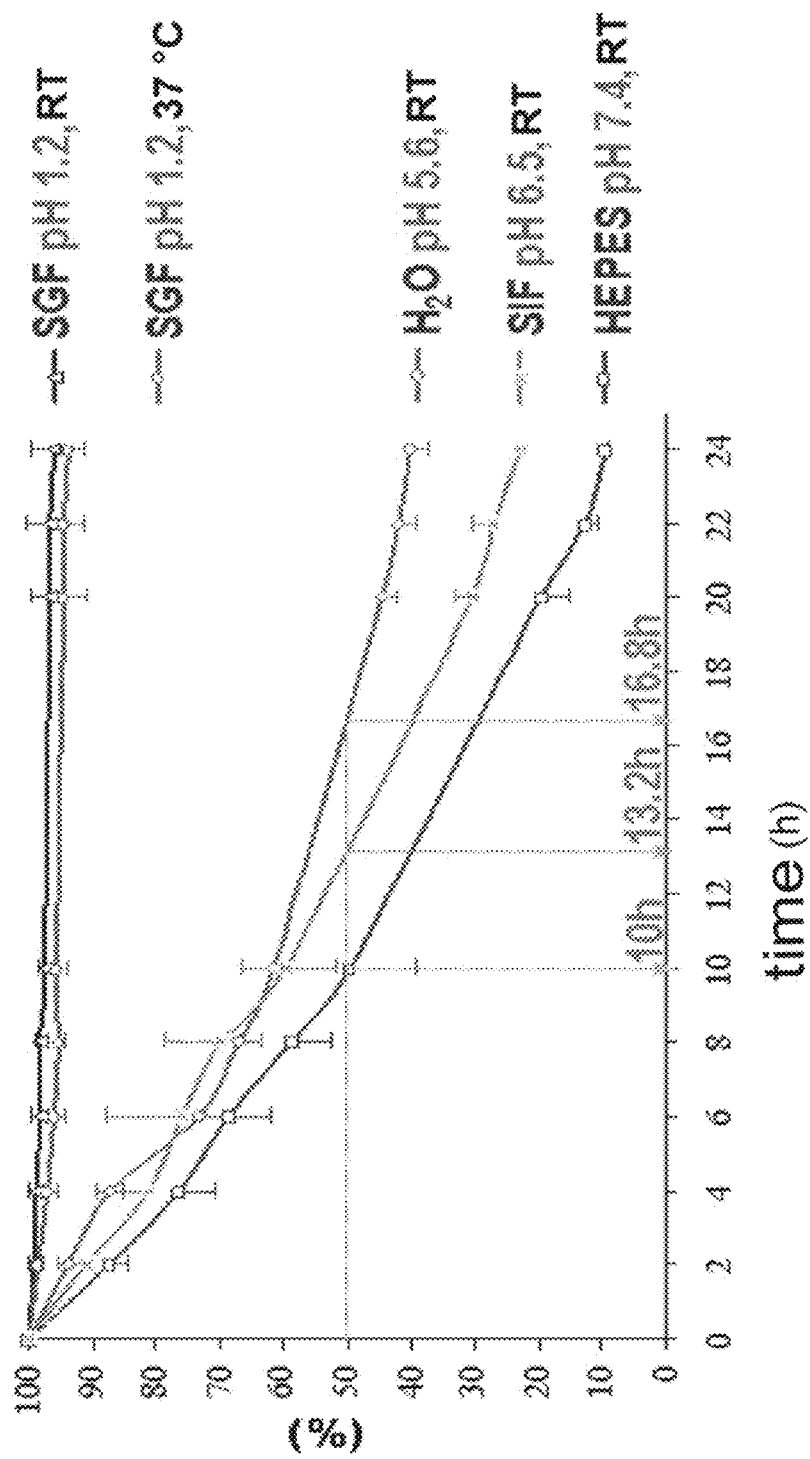
FIG. 7 shows the study of the stability of quercetin dissolved in aqueous medium [$H_2O$ at room temperature; aqueous medium at pH 7.4 at room temperature; simulated gastric fluid (SGF) at room temperature; simulated gastric fluid (SGF) at 37° C., simulated intestinal fluid (SIF) at room temperature] (A) and of the chemical stability of various concentrations (1, 2, 3, 4 and 5%) of quercetin encapsulated in the multicompartment lipid nanoparticles of the invention (B, right); the physical stability of the particles is shown at left in FIG. 7B.

To this end, the stability of quercetin in various fluids was quantified by means of an HPLC assay. The various fluids studied were simulated gastric fluid (SGF, US Pharmacopeia) at room temperature and at 37° C., simulated intestinal fluid (SIF, US Pharmacopeia), 10 mM HEPES buffer (pH 7.4) and room-temperature water. Samples taken over 24 hours showed in particular that in room-temperature water about 50% of the quercetin is degraded within 17 hours (FIG. 7A), whereas this molecule is more stable in more acidic fluids.

Figure 7B:
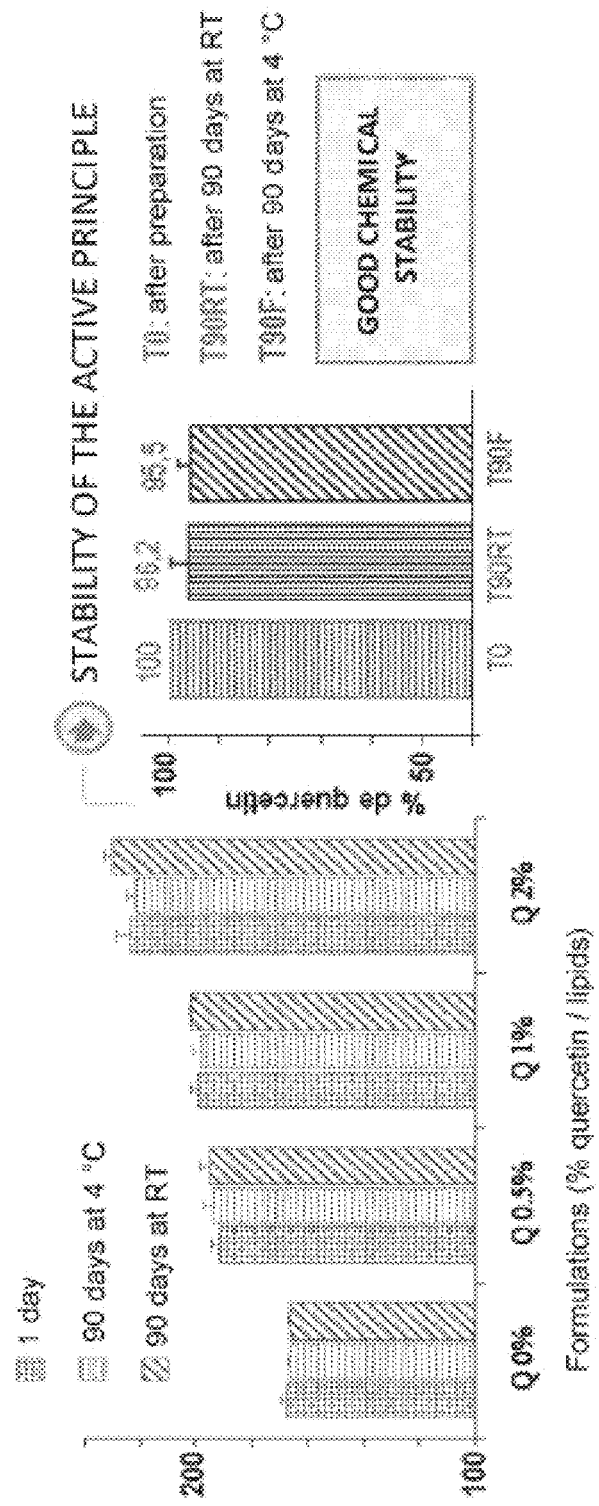

On the other hand, after encapsulation, storage as a suspension in water and ultracentrifugation, the assay of the nanoparticles showed that about 100% of the quercetin was still found after 90 days of preservation (FIG. 7B, right). Furthermore, the particles encapsulating the active principle remained physically stable for at least 90 days, at room temperature as at 4° C. (FIG. 7B, left).

Example 3: Preparation of Multicompartment Lipid Nanoparticles (Cellisomes)

Others cellisomes were obtained, according to the protocol described above, from various excipients.

For example, the lipid part was made of linoleoyl macrogol-6 glycerides (European Pharmacopoeia), oleoyl macrogol-6 glycerides (EP) or propylene glycol monolaurate (EP); the phospholipid was dipalmitoyl-phosphatidylcholine; the nonionic surfactant was stearoyl macrogol-32 glycerides (EP), a synthetic mixture of mono- and diesters of stearic acid and macrogol-32 (40/60 m/m), or polyoxyethylene (40) stearate.

Figure 1:
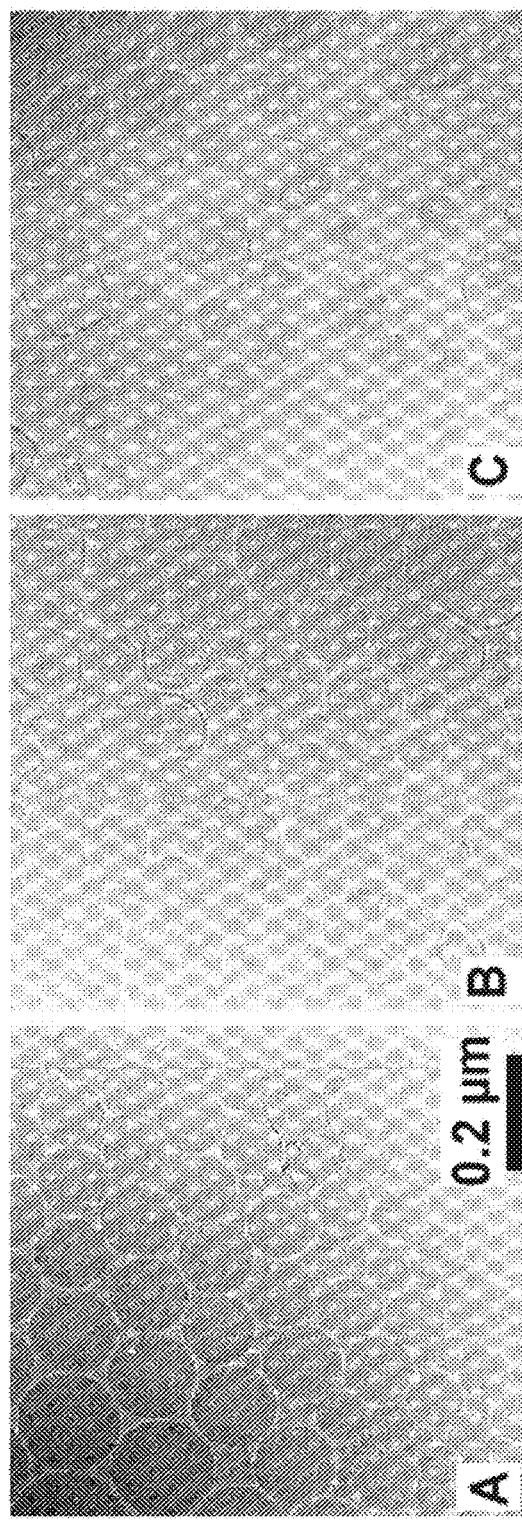
FIG. 1 shows electron microscope images of structures called "handbags" obtained under various operating conditions. Whatever said conditions, the proportion of "handbags" remains in the minority.
Figure 2:
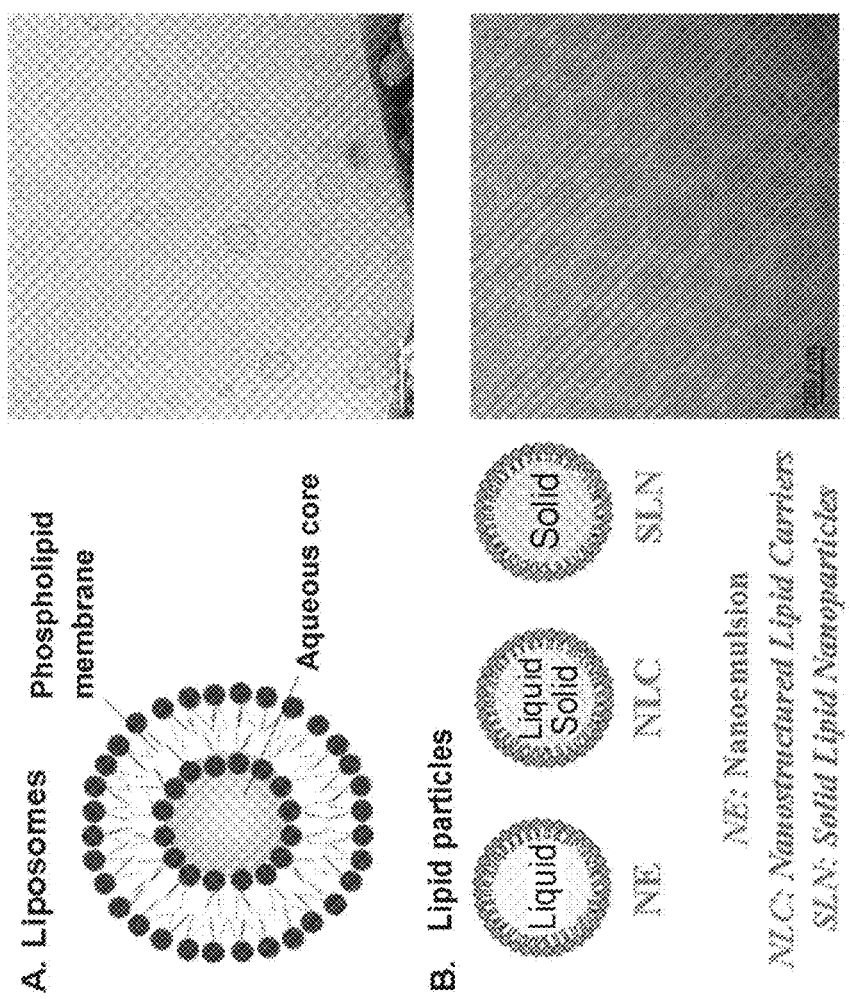
FIG. 2 shows the schematic descriptions and the cryonic transmission electron microscopy (cryo-TEM) images of the liposomes (A) and the lipid particles (B).
Figure 3:
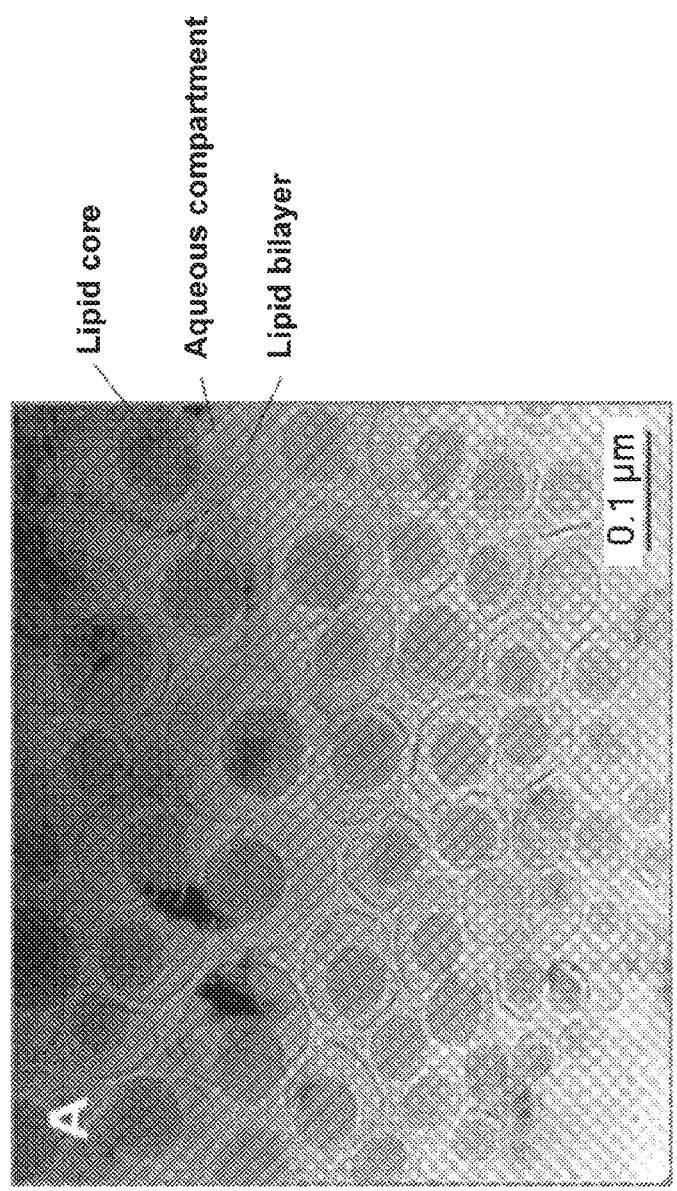
FIG. 3 shows a cryo-TEM image of the multicompartment lipid nanoparticles of the invention.
Figure 4A:
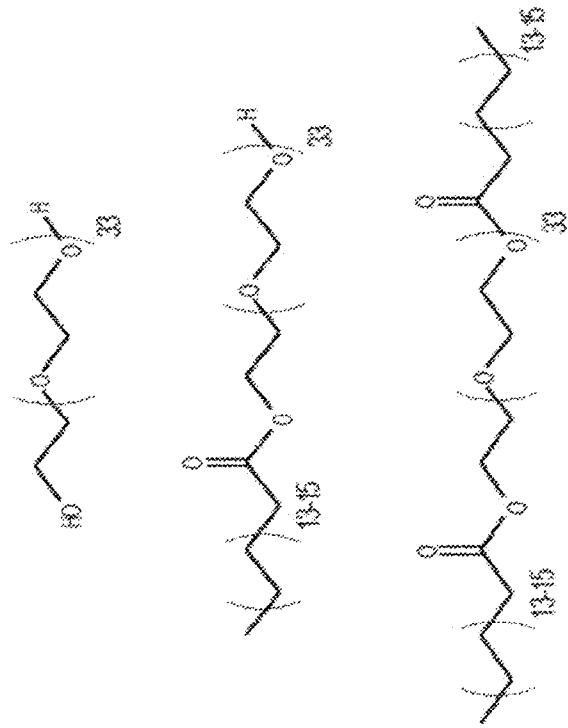
FIG. 4 shows the constituents of Gelucire® 50-13 (A) and a diagram of the membrane superstructure of the multicompartment lipid nanoparticles of the invention (B).
Figure 4A:
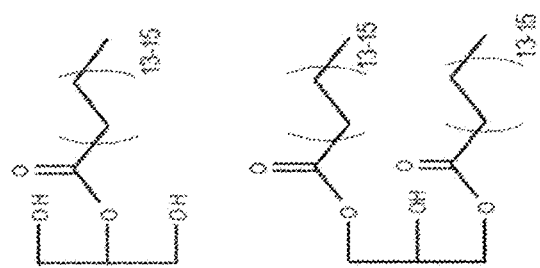
Figure 4A:
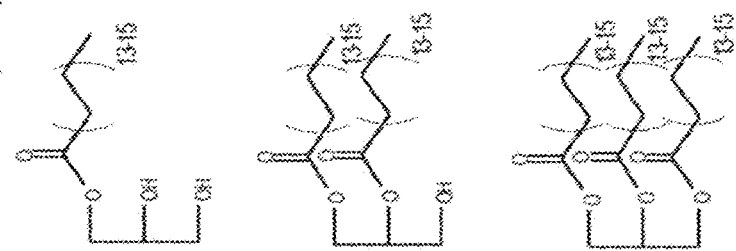
Figure 4B:
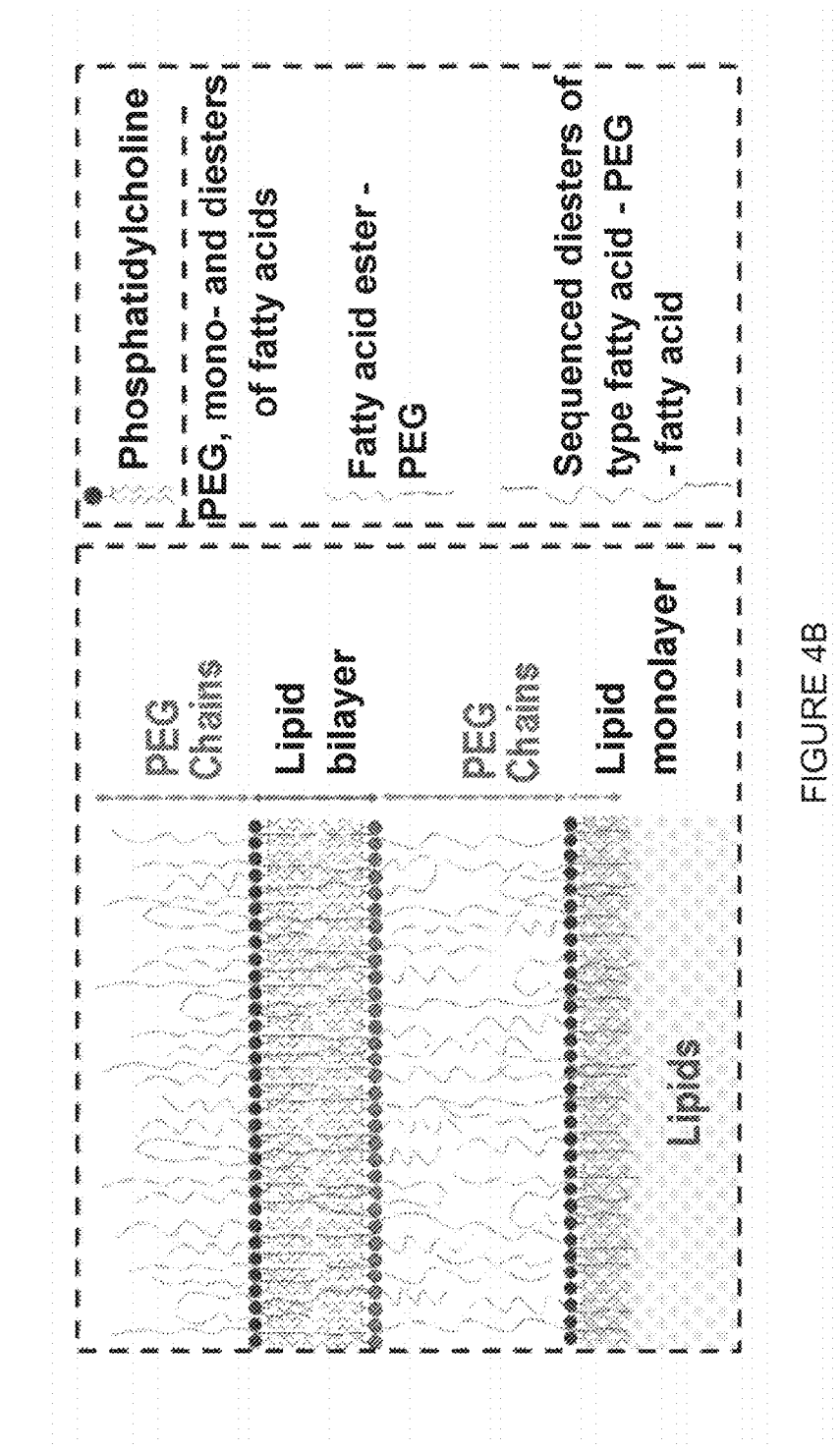

For the whole of these excipients, cryo-TEM observations confirmed that the nanoparticles are compartmented and of a morphology similar to that shown in FIG. 3.

Example 4: Preparation of a 10 g Batch of Multicompartment Lipid Nanoparticles (Cellisomes)

Preparation

The preparation of multicompartment lipid nanoparticles is depicted schematically in FIG. 5.

Nanodispersions were prepared using a single-stage homogenizer (HPH Laboratory, Stansted Fluid Power Ltd, England) fitted with a heating system and associated with an IKA T10 Ultra-Turrax (Janke & Kunkel GmbH & Co.KG, IKA®-Labotechnik, Germany) for preparation of the primary dispersion.

Ten grams of nanodispersions was prepared according to the protocol including the following three steps:

Dispersion:

First, the lipids and the surfactants (Gelucire® 50/13 and Phospholipon® 90G) were weighed and introduced into 7 ml and 20 ml flasks, respectively. The required amount of water was added to the flask containing the surfactants and then the surfactant suspension was prepared at 70° C. with mechanical agitation (IKA T10 Ultra-Turrax, Janke & Kunkel GmbH & Co.KG, IKA®-Labotechnik, Germany) at a speed of 8500 rpm for 5 minutes. Finally, the lipid mixture, also heated to 70° C., was added to the aqueous phase and agitated with the Ultra-Turrax at a speed of 20000 rpm for 5 minutes, to obtain an oil/water predispersion.

Particle Size Reduction and Homogenization Using HPH:

The dispersion obtained was quickly introduced into the single-stage homogenizer (HPH Laboratory, Stansted Fluid Power Ltd, England) preheated to 70° C. It underwent therein 4 homogenization cycles under a pressure of 1000 bars.

Cooling the Particles:

The nanodispersions were then maintained at room temperature.

Composition

The multicompartment lipid nanoparticles obtained by the preparation method described above comprise (% by mass):

| Labrafil ® M2125CS | 20% |
|---|---|
| Phospholipon 90G | 1% |
| Gelucire ® 50-13 | 2% |
| Water (q.s. ad) | 10 g |

Analysis of Size and Morphology

Following this preparation method, the nanoparticles have a hydrodynamic diameter of 228±2 nm. Furthermore, cryo-TEM observations confirm that the nanoparticles are compartmented and of a morphology similar to that shown in FIG. 3.

Example 5: A 10 g Batch of Multicompartment Lipid Nanoparticles (Cellisomes) as Carriers for Molecules of Pharmaceutical and/or Cosmetic Interest Multicompartment lipid nanoparticles were prepared according to the protocol described in Example 4 and tested for their ability to encapsulate various active principles.

For skin applications, molecules of dermocosmetic interest were selected according to their calculated octanol-water partition coefficient (Log P) their molar mass and then incorporated into the formulation. The three molecules were: caffeine (anti-cellulite; log P=−0.55, 194 g/mol), chloroxylenol (antiseptic; log P=3.30; 156 g/mol) and irgasan (disinfectant; log P=4.98; 289 g/mol).

These molecules of interest were dissolved in the aqueous phase, for hydrophiles, or in the lipid phase, for lipophiles, before being mixed by Ultra-Turrax in the protocol described in Example 3. Taking into account their solubility in the various fluid components of the compartmented nanoparticles, caffeine was introduced into the aqueous phase while chloroxylenol and irgasan were incorporated into the lipid phase.

The final concentration of each of the compounds of interest in the multicompartment nanoparticle dispersion is 1% by mass.

Analysis of Size and Morphology

Following this preparation method, the nanoparticles containing caffeine had a hydrodynamic diameter of 223±3 nm, remained stable for at least 12 days at 25° C., the nanoparticles containing irgasan had a hydrodynamic diameter of 224±4 nm, which remained stable for at least 12 days at 25° C., and the nanoparticles containing chloroxylenol had a hydrodynamic diameter of 245±2 nm, which remained stable for at least 1 month at 25° C.

For each incorporated molecule, cryo-TEM observations confirmed that the nanoparticles are compartmented and of a morphology similar to that shown in FIG. 3.

Example 6: Preparation of a Multicompartment Lipid Nanoparticle (Cellisome) Gel Multicompartment lipid nanoparticles were prepared according to the protocol described in Example 4.

Following this preparation, the compartmented nanoparticles were mixed with 2% Carbopol® 974 NF preformed gel neutralized with triethanolamine. Concentrated to 0.2% and 0.4% in Carbopol® 974 NF and containing 20.7% and 18.4% lipid excipients (by mass), respectively, the final gels retain the shear-thinning nature of Carbopol® 974 NF gels lacking nanoparticles.

Measurements of hydrodynamic diameters and cryo-TEM observations showed that the mixture with Carbopol® 974 NF did not change the size of the nanoparticles or their compartmented morphology, even after storage for 5 months at 25° C.

Example 7: Preparation of a 1 kg Batch of Multicompartment Lipid Nanoparticles (Cellisomes)

Preparation

The preparation of multicompartment lipid nanoparticles is depicted schematically in FIG. 5.

Nanodispersions were prepared using a two-stage homogenizer (APV 2000, Invensys, Albertslund, Denmark) fitted with a heating system and associated with a T18 Ultra-Turrax Basic (Janke & Kunkel GmbH & Co.KG, IKA®-Labotechnik, Germany) for preparation of the primary dispersion. One kilogram of nanodispersions was prepared according to the protocol including the following three steps:

Dispersion:

First, the lipids and the surfactants (Gelucire® 50/13 and Phospholipon® 90G) were weighed and introduced into 200 ml and 1000 ml beakers, respectively. The required amount of water was added to the beaker containing the surfactants and then the surfactant suspension was prepared at 70° C. with mechanical agitation (T18 Ultra-Turrax Basic, Janke & Kunkel GmbH & Co.KG, IKA®-Labotechnik, Germany) at a speed of 11000 rpm for 15 minutes. Finally, the lipid mixture, also heated to 70° C., was added to the aqueous phase and agitated with the Ultra-Turrax at a speed of 20000 rpm for 15 minutes, in order to obtain an oil/water predispersion.

Particle Size Reduction and Homogenization Using HPH:

The dispersion obtained was introduced into the two-stage homogenizer (APV 2000, Invensys, Albertslund, Denmark) preheated to 70° C. and maintained with mechanical agitation using a Rayneri 1144 mixer (800 rpm). It underwent therein several continuous homogenization cycles for 15 minutes, under a double effect of pressure (the pressure of the $1^{st}$ step is 600 bar and that of the $2^{nd}$ step is 200 bar), to form a hot oil/water nanodispersion.

Cooling the Particles:

The nanodispersions were then packaged in 20 ml flasks and maintained at room temperature.

Composition

The multicompartment lipid nanoparticles obtained by the preparation method described above comprise (% by mass):

| | |
|---|---|
| Labrafil ® M2125CS | 20% |
| Phospholipon 90G | 1% |
| Gelucire ® 50-13 | 2% |
| Water (q.s. ad) | 1 kg |

Analysis of Size and Morphology

Following this preparation method, cryo-TEM observations confirmed that the nanoparticles were compartmented and of a morphology similar to that shown in FIG. 3.

The invention claimed is:

1. Multi-compartment lipid nanoparticles having a mean diameter of 10 to 500 nm, wherein the multi-compartment lipid nanoparticles comprise a first lipophilic compartment comprising lipids partly enclosed by a second hydrophilic compartment delimited by a phospholipid bilayer, said first compartment being partly anchored to said second compartment, and
   wherein the multi-component lipid nanoparticles are stabilized by a mixture of surfactants comprising (a) phospholipids and (b) a mixture of non-ionic surfactants comprising a three-sequence surfactant of "hydrophobic-hydrophilic-hydrophobic" type having a Griffin HLB value of greater than 11,
   wherein the composition does not include a cationic surfactant.

2. The nanoparticles of claim 1, where the polydispersity index is 5 to 15%.

3. The nanoparticles of claim 1, where the mean diameter is 100 to 250 nm.

4. The nanoparticles of claim 1 where the lipids of the lipophilic compartment are in liquid or semi-solid state at 25° C.

5. The nanoparticles of claim 1, where the lipophilic compartment comprises a fatty acid ester optionally mixed with a glyceride.

6. The nanoparticles of claim 5, where said fatty acid ester comprises mixtures of polyethylene glycol mono- and diesters, the molar mass of the hydrophilic part of which varies from 100 to 700 g/mol.

7. The nanoparticles of claim 5, where the glyceride is selected from the group consisting of mixtures of glycerol mono-, di- and triesters that are liquid or solid at 25° C.

8. The nanoparticles of claim 1, where said phospholipid surfactant (a) comprises mixtures of zwitterionic phospholipids.

9. The nanoparticles of claim 1, further comprising at least one molecule of interest.

10. The nanoparticles of claim 9, where the molecule of interest is selected from the group consisting of a nucleic acid, a protein, a polysaccharide and a molecule of 40 to 2000 Da.

11. Pharmaceutical composition comprising a suspension of nanoparticles as defined in claim 1 in a pharmaceutically acceptable excipient.

12. The nanoparticles of claim 1 for use as a carrier for administering a molecule of interest.

13. The nanoparticles of claim 9 for use as medicine.

14. The nanoparticles of claim 13, wherein said medicine is administered by injection, orally, cutaneously, or nasally.

15. The nanoparticles of claim 1, wherein the three-sequence surfactant comprises a macrogoglyceride or a polyoxyethylene fatty acid ester.

16. Method for preparing the multicompartment lipid nanoparticles of claim 1 comprising the following steps:
   preparation of an oil/water emulsion comprising water, at least one lipid, phospholipids, a mixture of nonionic surfactants comprising a three-sequence surfactant of "hydrophobic-hydrophilic-hydrophobic" type, and optionally at least one molecule of interest;
   homogenization of said emulsion under high pressure.

17. Method as claimed in claim 16, further comprising a step of heating the emulsion to a temperature of 30 to 80° C. before its homogenization.

18. Method as claimed in claim 16, where said lipid comprises mixtures of polyethylene glycol mono- and diesters, the molar mass of the hydrophilic part of which varies from 100 to 700 g/mol.

19. Method as claimed in claim 16, where said phospholipid comprises mixtures of zwitterionic phospholipids.

20. Method as claimed in claim 16, where said mixture of hydrophilic nonionic surfactants comprises macrogolglycerides or polyoxyethylene fatty acid esters.

21. Method as claimed in claim 20, where the oil/water emulsion comprises:
- 5-30% by mass lipids;
- 0.5-5% by mass phospholipids;
- 0.5-5% by mass of said mixture of hydrophilic nonionic surfactants comprising macrogoglycerides or polyoxyethylene fatty acid esters.

* * * * *